US011547981B2

(12) United States Patent
Schwab et al.

(10) Patent No.: US 11,547,981 B2
(45) Date of Patent: Jan. 10, 2023

(54) METHOD FOR PRODUCING TRANSITION ALUMINA CATALYST MONOLITHS

(71) Applicant: BASF SE, Ludwigshafen am Rhein (DE)

(72) Inventors: Matthias Georg Schwab, De Meern (NL); Esther Groeneveld, De Meern (NL); Peter Berben, De Meern (NL); Harry Bouwman, De Meern (NL); Willem Dijkstra, De Meern (NL); Bart Michielsen, Mol (BE); Jasper Lefevere, Mol (BE)

(73) Assignee: BASF SE

( * ) Notice: Subject to any disclaimer, the term of this patent is extended or adjusted under 35 U.S.C. 154(b) by 0 days.

(21) Appl. No.: 15/733,841

(22) PCT Filed: May 28, 2019

(86) PCT No.: PCT/EP2019/063815
§ 371 (c)(1),
(2) Date: Nov. 30, 2020

(87) PCT Pub. No.: WO2019/229061
PCT Pub. Date: Dec. 5, 2019

(65) Prior Publication Data
US 2021/0213423 A1   Jul. 15, 2021

(30) Foreign Application Priority Data
May 29, 2018  (EP) .................................... 18174925

(51) Int. Cl.
| | |
|---|---|
| B01J 21/04 | (2006.01) |
| B33Y 10/00 | (2015.01) |
| B29C 64/106 | (2017.01) |
| B01J 35/00 | (2006.01) |
| B01J 35/04 | (2006.01) |
| B01J 35/06 | (2006.01) |
| B01J 35/10 | (2006.01) |
| B01J 37/00 | (2006.01) |
| B01J 37/04 | (2006.01) |
| B01J 37/08 | (2006.01) |
| B28B 1/00 | (2006.01) |
| B28B 11/24 | (2006.01) |
| C07C 1/24 | (2006.01) |
| C07C 5/27 | (2006.01) |
| B33Y 70/00 | (2020.01) |

(Continued)

(52) U.S. Cl.
CPC ............ *B01J 21/04* (2013.01); *B01J 35/002* (2013.01); *B01J 35/04* (2013.01); *B01J 35/06* (2013.01); *B01J 35/1014* (2013.01); *B01J 35/1019* (2013.01); *B01J 35/1038* (2013.01); *B01J 35/1042* (2013.01); *B01J 35/1047* (2013.01); *B01J 35/1085* (2013.01); *B01J 35/1095* (2013.01); *B01J 37/00* (2013.01); *B01J 37/0018* (2013.01); *B01J 37/04* (2013.01); *B01J 37/088* (2013.01); *B28B 1/001* (2013.01); *B28B 11/243* (2013.01); *B29C 64/106* (2017.08); *B33Y 10/00* (2014.12); *C07C 1/24* (2013.01); *C07C 5/2705* (2013.01); *B29K 2509/02* (2013.01); *B33Y 70/00* (2014.12); *B33Y 80/00* (2014.12); *C07C 2521/04* (2013.01)

(58) Field of Classification Search
None
See application file for complete search history.

(56) References Cited

U.S. PATENT DOCUMENTS

| | | |
|---|---|---|
| 6,027,326 A | 2/2000 | Cesarano et al. |
| 6,401,795 B1 | 6/2002 | Cesarano et al. |
| 6,993,406 B1 | 1/2006 | Cesarano et al. |

(Continued)

FOREIGN PATENT DOCUMENTS

| | | |
|---|---|---|
| EP | 2231559 A1 | 9/2010 |
| WO | 2009/074461 A1 | 6/2009 |

(Continued)

OTHER PUBLICATIONS

International Preliminary Report on Patentability received for PCT Patent Application No. PCT/EP2019/063815, dated Aug. 21, 2020, 34 pages.

(Continued)

*Primary Examiner* — Colin W. Slifka
(74) *Attorney, Agent, or Firm* — Faegre Drinker Biddle & Reath LLP

(57) ABSTRACT

A method for producing a three-dimensional porous transition alumina catalyst monolith of stacked catalyst fibers, comprising:
a) Preparing a paste in a liquid diluent of hydroxide precursor particles and/or oxyhydroxide precursor particles of transition alumina particles, all particles in the suspension having a number average particle size in the range of from 0.05 to 700 μm,
b) extruding the paste nozzle(s) to form fibers, and depositing the extruded fibers to form a three-dimensional porous catalyst monolith precursor,
c) drying the precursor to remove the liquid diluent,
d) performing a temperature treatment of the dried porous catalyst monolith precursor to form the transition alumina catalyst monolith,
wherein no temperature treatment of the porous catalyst monolith precursor or porous catalyst monolith at temperatures above 1000° C. is performed and wherein no further catalytically active metals, metal oxides or metal compounds are applied to the surface.

23 Claims, No Drawings

(51) Int. Cl.
  *B33Y 80/00*     (2015.01)
  *B29K 509/02*    (2006.01)

(56) References Cited

U.S. PATENT DOCUMENTS

| | | | |
|---|---|---|---|
| 7,351,393 | B1 | 4/2008 | Bayense et al. |
| 7,527,671 | B1 | 5/2009 | Stuecker et al. |
| 8,119,554 | B2 | 2/2012 | Kashani-Shirazi et al. |
| 9,272,264 | B2 | 3/2016 | Coupland |
| 2005/0109241 | A1* | 5/2005 | Addiego ............ C04B 35/6365 106/692 |

FOREIGN PATENT DOCUMENTS

| | | |
|---|---|---|
| WO | 2016/097760 A1 | 6/2016 |
| WO | 2016/166523 A1 | 10/2016 |
| WO | 2017/055565 A1 | 4/2017 |
| WO | 2018/099956 A1 | 6/2018 |

OTHER PUBLICATIONS

International Search Report and Written Opinion received for PCT Patent Application No. PCT/EP2019/063815, dated Jul. 17, 2019, 23 pages.
Danaci et al.: "Efficient CO2 methanation over Ni/Al2O3 coated structured catalysts", Catalysis Today, 273 (2016), pp. 234-243.
John N. Stuecker et al.: "Advanced Support Structures for Enhanced Catalytic Activity", Industrial & Engineering Chemistry Research, vol. 43, No. 1, Jan. 1, 2004, pp. 51-55, XP055415171.
Keith Hudson L et al.: "Aluminum Oxide", Internet Citation, Jun. 15, 2000, pp. 1-40, XP002596245,.
Tubio Carmen R et al.: "3D printing of a heterogeneous copper-based catalyst", Journal of Catalysis, Academic Press, Duluth, MN, US, vol. 334, Dec. 30, 2015, pp. 110-115, XP029391133.
Xintong Zhou et al: "Three-dimensional Printing for Catalytic Applications: Current Status and Perspectives", Advanced Functional Materials, vol. 27, No. 30, Aug. 1, 2017, p. 1701134, XP055522385.

* cited by examiner

METHOD FOR PRODUCING TRANSITION ALUMINA CATALYST MONOLITHS

CROSS-REFERENCE TO RELATED APPLICATIONS

This application is a national stage application (under 35 U.S.C. § 371) of PCT/EP2019/063815, filed May 28, 2019, which claims benefit of European Application No. 18174925.0, filed May 29, 2018, both of which are incorporated herein by reference in their entirety.

The invention relates to a method for producing a three-dimensional porous transition alumina catalyst monolith of stacked catalyst fibers, the thus obtained monolith and its use.

Typically, inorganic catalysts are produced as powders and as shaped bodies in the form of extrudates, granules, pellets, spheres, tablets or extruded monolith or honeycomb structures.

Current commercial catalyst shaped bodies are limited by their size. The smallest available commercial size is approximately 1.2 mm (for extrudates). It has advantages for certain catalytic applications to use smaller diameter extrudates due to increased geometric surface area and shorter pore diffusion lengths. However, such smaller extrudates cannot be used in commercial reactors set-ups due to too low strength and too high pressure drop. For multi-tubular reactors it is required to fill reactor tubes very homogenously with a catalyst material. To ensure reactor balance, today's catalysts rely on cut extrudates or tablets to ensure homogeneous particle size. Likewise, the loading of such reactors is time-consuming and labor- and cost-intensive. It would be desirable to fill reactors, especially multi-tubular reactors with shaped bodies of identical size and shape and enhanced mechanical properties. For today's alumina catalysts (e.g. for dehydration reactions) such shaped bodies offering the combination of these advantages are not known.

Transition alumina catalysts may be employed as extrudates with standard diameters ranging from 1.2 mm to 12.0 mm. Special cross sections such as stars, trilobes, quadrolobes and ring-type geometries are possible. Alternatively, tablets having a diameter between 1.5 and 20.0 mm are employed. The different catalyst shapes lead to different pressure drops in the reactor.

Alternative processes which allow for a greater variety of shapes in comparison to a linear stretched honeycomb structure can be prepared e.g. by rapid prototyping processes. The process described in U.S. Pat. No. 8,119,554, for example, involves the production of a shaped body by means of a powder-based rapid prototyping process, in which a binder material is selectively introduced in an inorganic catalyst powder to form the three-dimensional structure. Alumina is listed among the suitable metal oxides.

A further production process often named robocasting can be employed. In this method, a paste of the catalyst material particles is extruded into strands which are deposited in stacked layers to form the desired three-dimensional structure. Subsequently, the structure is dried and heat treated. The production of regenerable diesel soot particulate filters by robocasting methods is disclosed in U.S. Pat. No. 7,527,671.

This method has also been employed for preparing Cu/alumina catalytic systems with a wood pile porous structure. Journal of Catalysis 334 (2016), 110 to 115, relates to the 3D printing of a heterogeneous copper-based catalyst. Alumina powder with a mean particle size of 0.5 µm was added to an aqueous solution of copper(II) nitrate, and the viscosity of the resulting suspension was adjusted by adding hydroxypropyl methyl cellulose as viscosity modifier. The resulting ink was concentrated by the removal of water by evaporation until suitable for extrusion. The aqueous ink was loaded into a syringe attached by a nozzle with a diameter of 410 µm. A robotic deposition system was used to create the woodpile structures. The structure was dried at room temperature for 24 h and subsequently sintered at 1400° C. for 2 h in air.

Ni/alumina-coated structured catalysts are disclosed in Catalysis Today, 273 (2016), pages 234 to 243. To prepare the catalyst, stainless steel supports were prepared using the robocasting process. The resulting 3D structures were sintered at 1300° C. for 4 h and a coating slurry of boehmite powder with nickel loading was applied. Thus, only the stainless steel support structure was prepared by robocasting.

WO 2016/166523 discloses in example 1 a catalyst comprising particles formed from alumina and manufactured during an additive layer manufacturing method using a 3D printer. The particles were coated with a slurry containing a solid commercial oxidation catalyst formulation. The catalyst has a length of 5.4 mm and a diameter of 6.0 mm.

Ind. Eng. Chem. Res., Vol. 43, No. 1, 2004, pages 51 to 55 discloses a robocast monolith of dimensions 12.7 mm×22 mm prepared from alumina and sintered to more than 99% density at 1615° C. The monolith is employed as ceramic support structure.

U.S. Pat. No. 9,272,264 discloses a dodecahedral frame structure prepared from alumina using a Phenix Systems PX series laser sintering machine. After removing the parts from the powder bed they are sintered at a temperature up to about 1800° C., see example 2.

U.S. Pat. No. 6,993,406 discloses a robocasting process in which materials that can be used include alumina. The process is used for preparing bio-compatible scaffolds.

All the above-mentioned processes employ a heat treatment step at temperatures well above 1000° C. which is typically used to synthesize low- or non-porous materials.

In general, at temperatures of above 1000° C., for example 1150° C. and above, alpha-alumina is obtained which has a low surface area and can be typically only employed as a catalyst support or refractive material, but not as catalytically active material itself. Due to the high-temperature treatment applied in the synthesis of alpha-alumina, most of the functional groups, acidic and basic in nature, will be lost.

On the contrary, transition alumina can be obtained at intermediate temperatures between 500° C. and 1000° C. Functional groups are found in transition alumina catalysts and are at the origin of their catalytic activity. The surface chemistry of transition alumina catalysts is highly complex and involves Bronsted and Lewis acidity and basicity.

Thus, heat treatment at high temperatures is detrimental to the catalyst properties. Typically, also the pore volume and surface area deteriorate upon this temperature treatment.

Aluminum oxide can occur in various crystallographic phases and commercial catalyst systems may consist of a single crystallographic phase or mixtures of two or more crystallographic phases.

Commercial catalyst systems are most often derived from transition alumina phases but not from alpha-alumina.

Suitable transition alumina modifications are gamma-, delta-, theta-, chi-, kappa-, rho- or eta-alumina or mixtures thereof.

The exact crystalline nature of the transition alumina catalyst will be determined by both the initial crystalline properties of the hydroxide or oxyhydroxide precursors and the thermal process and calcination temperature to which the catalyst is subjected during its manufacture.

Calcining temperatures are typically between 500° C. and 1000° C. This process results in the loss of physically and chemically bound water.

Optionally, steam may be applied during the calcination step to further modify the properties of the transition alumina catalyst.

The following scheme shows the formation of transition alumina phases and alpha-alumina:

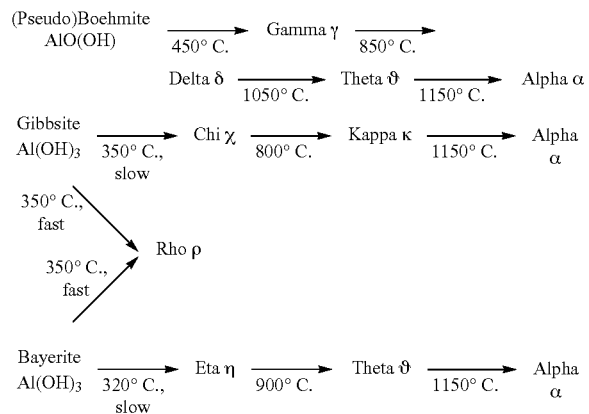

Hydroxide precursors suitable for the synthesis of transition alumina catalysts comprise gibbsite, bayerite, nordstrandite and doyleite.

Oxyhydroxide precursors suitable for the synthesis of transition alumina catalysts comprise diaspore, boehmite, pseudoboehmite and akdalaite or tohdite.

Although the common transition aluminas are often derived from hydroxide or oxyhydroxide precursors obtained from the Bayer process and find many catalytic applications, high-purity precursor materials (e.g. pseudoboehmite from the Ziegler process, for linear alcohol production) are sometimes preferred.

For the synthesis of transition alumina catalysts also mixtures of different hydroxide precursors, mixtures of different oxyhydroxide precursors or mixtures of hydroxide and oxyhydroxide precursors may be applied.

To modify the surface properties, acidity and alkalinity of transition alumina catalysts ("doping") other element precursors may be included on purpose in a range of 0.1 wt % to 10.0 wt %, based on their content in the final transition alumina.

To obtain high external surface areas for the catalysts, e.g. for diffusion limited reactions, or high packing densities with low void volume, in fixed-bed catalyst reactors, the use of smaller catalyst particles would be necessary. In mass-transfer limited reactions the performance of small catalyst particles is better than that of larger extrudates. A disadvantage, however, is that smaller extrudates show a higher pressure drop in the packed bed which will limit their application in chemical reactors. Furthermore, the mechanical strength of these small extrudates is typically not sufficient to form a packed bed reactor on commercial scale.

The object underlying the present invention is to provide a transition alumina catalyst which has a high external surface area or high packing density. The catalyst structure should be sufficiently mechanically stable so that packed catalyst beds can be formed in a reactor, which show a low pressure drop.

The object is achieved according to the present invention by a method for producing a three-dimensional porous transition alumina catalyst monolith of stacked catalyst fibers, comprising the following steps:
a) Preparing a suspension paste in a liquid diluent of transition alumina particles, hydroxide precursor particles or oxyhydroxide precursor particles or mixtures thereof and which suspension can furthermore comprise a binder material, a plasticizer and optionally a dopant, all particles in the suspension having a number average particle size in the range of from 0.5 to 500 μm,
b) extruding the paste of step a) through one or more nozzles to form fibers, and depositing the extruded fibers to form a three-dimensional porous catalyst monolith precursor,
c) drying the porous catalyst monolith precursor to remove the liquid diluent,
d) performing a temperature treatment of the dried porous catalyst monolith precursor of step c) at a temperature in the range of from 500 to 1000° C., to form the transition alumina catalyst monolith,
wherein no temperature treatment of the porous catalyst monolith precursor or porous catalyst monolith at temperatures above 1000° C. is performed and wherein no further catalytically active metals, metal oxides or metal compounds are applied to the surface of the catalyst monolith precursor or transition alumina catalyst monolith. Preferably, also no further catalytically active metals, metal oxides or metal compounds are present in the suspension paste.

Specifically, the present invention relates to a method for producing a three-dimensional porous transition alumina catalyst monolith of stacked catalyst fibers, comprising the following steps:
a) Preparing a suspension paste in a liquid diluent of hydroxide precursor particles or oxyhydroxide precursor particles of transition alumina particles or mixtures thereof and which suspension can furthermore comprise a binder material in a maximum amount of 20 wt %, based on the amount of hydroxide precursor particles or oxyhydroxide precursor particles of transition alumina particles or mixtures thereof and/or a plasticizer and/or a dopant in a maximum amount of 10 wt %, based on the amount of hydroxide precursor particles or oxyhydroxide precursor particles of transition alumina particles or mixtures thereof, all particles in the suspension having a number average particle size in the range of from 0.05 to 700 μm,
b) extruding the paste of step a) through one or more nozzles to form fibers, and depositing the extruded fibers to form a three-dimensional porous catalyst monolith precursor,
c) drying the porous catalyst monolith precursor to remove the liquid diluent,
d) performing a temperature treatment of the dried porous catalyst monolith precursor of step c) at a temperature in the range of from 500 to 1000° C., to form the transition alumina catalyst monolith,
wherein no temperature treatment of the porous catalyst monolith precursor or porous catalyst monolith at temperatures above 1000° C. is performed and wherein no further catalytically active metals, metal oxides or metal compounds are applied to the surface of the transition alumina precursor particles, the catalyst monolith precursor or transition alumina catalyst monolith, and wherein (besides the dopant) preferably no further catalytically active metals, metal oxides or metal compounds are present in the suspension paste. The monolith is preferably for use in dehydration reactions. Preferred dehydration reactions are outlined below.

Transition alumina precursor particles are employed in step a), and the precursor component in the porous catalyst monolith precursor is transformed in step d) to form the transition alumina and thus the transition alumina catalyst monolith. The temperature treatment in step d) can increase the mechanical strength and cohesion of the monolith and also helps to remove plasticizer and/or organic binders, consequently, since transition alumina precursor particles and optionally a binder and/or a plasticizer and/or a dopant are employed in step a), the precursor component in the porous catalyst monolith precursor is transformed to form the transition alumina catalyst monolith.

Thus, is step a) hydroxide precursor particles or oxyhydroxide precursor particles for transition alumina particles are employed.

In this respect, a three-dimensional monolith is a one-piece structure made of at least two stacked layers of fibers.

Step b) is preferably controlled by a control system data set or CAD file as described below, preferably implemented on a computer system.

According to the present invention, it has been found that hydroxide precursor particles or oxyhydroxide precursor particles of transition alumina particles can be employed in a robocasting process, wherein no heat treatment at temperatures above 1000° C. is performed in order to obtain mechanically stable catalytically active transition alumina structures which show a low pressure drop and high packing density.

The current invention allows to synthesize a catalyst shaped body based on transition alumina with high external surface area and high strength. The high external surface area is obtained by avoiding high temperature treatment and by producing small fibers having preferably a diameter of less than 1.2 mm which can be stacked into a 3D structure which can be a continuous fiber or composed of stacked discontinuous fibers that can be used in commercial applications.

The present invention leads to higher conversion levels and selectivity levels of the transition alumina catalysts resulting in better product yields. The low pressure drop also enables to increase the mass flow rates and achieve higher throughput per hour again resulting in better product yields and space time yields. It also enables to carry out chemical reactions at lower reaction temperatures, which is beneficial for better process economics. It furthermore enables reduced coke formation and less catalyst ageing due to shorter diffusion pathways and shorter residence times. Should coke formation occur over the course of the operation of the catalyst, a faster burn off of the carbon for example with hot air or steam is facilitated and less time is required for such regeneration which is beneficial for process economics. Furthermore, new reactors can be designed that are smaller than current set-ups leading to lower investment costs while maintaining the current output (process intensification). In the case of multi-tubular reactors, the loading can be made faster and a more reliable process operation is expected.

Preferably, in the method according to the present invention, no temperature or heat treatment at temperatures above 1000° C., more preferably above 975° C. is performed. The process step c) and the process step d) are preferred at temperatures not exceeding 950° C. Most preferably, the transformation of the hydroxide precursor component or oxyhydroxide precursor component or mixtures thereof in the porous catalyst monolith precursor to form the transition alumina catalyst monolith is performed at a temperature in the range of from 500 to 925° C.

The drying in step c) is preferably performed at a temperature in the range of from −100 to less than 500° C., more preferably 0 to 300° C., most preferably 20 to 150° C.

Step d) is preferably performed at a temperature in the range of from 500 to 925° C. and for a duration of 5 to 120 minutes.

In the method according to the invention, precursors of transition alumina particles are present in the suspension paste, specifically hydroxide precursor particles or oxyhydroxide precursor particles or mixtures thereof as described above. Preferably only precursors are employed and no transition alumina particles or only minor amounts thereof, e.g. a maximum of 10 wt %, preferably a maximum of 3 wt %, based on the amount of hydroxide precursor particles or oxyhydroxide precursor particles of transition alumina particles or mixtures thereof. If hydroxide precursor particles or oxyhydroxide precursor particles or mixtures thereof are present in the suspension paste, preferably in step d) a temperature treatment in the range of from 500 to 925° C. is performed to effect the transformation to transition alumina.

The method according to the present invention leads to a three-dimensional porous transition alumina catalyst monolith wherein no further catalytically active metals, metal oxides or metal compounds are applied to the surface of the precursor particles, the catalyst monolith precursor or a transition alumina catalyst monolith and preferably also are not present in the suspension paste. Thus, alumina, specifically transition alumina modifications are preferably the sole catalytically active material and at the same time the sole material forming the catalyst monolith.

Consequently, the catalyst monolith does not contain any surface coating like a wash coat often employed in prior art processes. The bulk transition alumina material forming the catalyst monolith is the catalytically active material per se.

If intended, minor amounts of dopants or mixtures of dopants, e.g. selected from chemical compounds of Li, Na, K, Ca, Mg, Ba, B, Ga, Si, Ti, Zr, Fe, W, P or Zn can be present in the suspension paste in a maximum amount of 10 wt %, based on the amount of hydroxide precursor particles or oxyhydroxide precursor particles of transition alumina particles or mixtures thereof, for example 0.1 to 10 wt %, preferably 1.0 to 5.0 wt %, based on the particles forming the transition alumina. Preferably no dopants are employed or added to the suspension.

The final transition alumina or the precursors thereof may also—inadvertently!—contain minor amounts of impurities which may qualify as dopants. In such cases, typical impurities are $Li_2O$, $Na_2O$, $K_2O$, CaO, MgO, BaO, $B_2O_3$ $Ga_2O_3$, $SiO_2$, $TiO_2$, $ZrO_2$, ZnO, $Fe_2O_3$ as well as chlorides, nitrates and sulfates. If doping is not intended—as it is preferred—, these amounts should be as low as possible. Typically for such cases, in the final transition alumina, preferably eta-, gamma-, or delta-alumina, the amount of such impurities is not higher than 5%, more preferably not higher than 2.5%, specifically not higher than 0.5 wt %, based on the transition alumina in the monolith or based on the amount of hydroxide precursor particles or oxyhydroxide precursor particles of transition alumina particles or mixtures thereof. In specific embodiments which are preferred, the content of impurities will be below 0.1 wt %, e.g. in case of ultrapure transition aluminas or high-purity precursor materials, and no dopant is employed or added to the suspension.

Thus, the catalyst monolith preferably does not contain additional catalytically active components like catalytically active metals in the final catalyst monolith.

The catalyst monolith obtained in the method of the invention is a transition alumina catalyst monolith. Transition alumina is different from alpha-alumina and includes gamma-, delta-, theta-, chi-, kappa-, rho- or eta-phases as shown above. Preferably, the transition alumina is predominantly or fully eta- or gamma- or delta-alumina. Thus, in one embodiment the major part of the alumina in the catalyst monolith is eta-, gamma- or delta-alumina. Minor amounts of other alumina phases can be present. Preferably, at least 80 wt % of the catalyst monolith are formed of transition alumina, preferably eta-, gamma-, or delta-alumina, more preferably at least 90 wt %, most preferably at least 99 wt %. Most preferably, transition alumina, preferably eta-, gamma- or delta-alumina is the sole phase forming the catalyst monolith.

The content of alpha-alumina in the final transition alumina catalyst monolith is preferably as low as possible. Preferably, the amount of alpha-alumina in the catalyst monolith is less than 10 wt %, more preferably less than 5 wt %, most preferably less than 1 wt %, based on the total weight of the catalyst monolith. Most preferably only traces of alpha-alumina or no alpha-alumina at all are present in the catalyst monolith.

The BET surface area, as determined by single point adsorption using the BET equation (as e.g. described by G. Sandstede et. al., Chem. Ing. Tech. 32 (1960), 413), should be at least 10 $m^2/g$. This coincides with the requirement of using a transition alumina, i.e. not an alpha-alumina. Suitable aluminas are the various transition aluminas including gamma-, delta-, theta-, chi-, kappa-, rho- or eta-alumina. These aluminas have a large BET surface area, generally in the range of 10 up to more than 500 $m^2/g$.

The final catalyst monolith preferably has a surface area in the range of from 10 to 500 $m^2/g$, more preferably 25 to 400 $m^2/g$, most preferably 50 to 350 $m^2/g$. The surface area is preferably determined by the single point BET method.

The pore volume is a further important requirement, whereby it is important that the total pore volume, as determined by mercury intrusion or nitrogen physisorption, is sufficiently high. In absolute terms the total pore volume should be at least 0.05 ml/g.

In specific embodiments, it may be desirable that the pore volume in pores of over 50 nm, more preferably over 250 nm and most preferably over 500 nm forms a substantial portion of the total pore volume.

In specific embodiments the ratio of the pore volume in pores of over 50 nm to total pore volume should preferably be more than 3%. An alumina having those characteristics has good reactant accessibility, which makes it very suitable for catalytic reactions requiring good diffusion of reactants and products through the alumina catalyst, thereby eliminating diffusion limitation problems as much as possible.

The pore volume and pore size distribution are determined by mercury porosimetry measurements, as described by J. Rouquerol et al. in Pure & Applied Chem., 66(8), 1994, pages 1752 to 1753, using the Washburn equation. Nitrogen physisorption is described by F. Schüth et al. in Handbook of Porous Solids, Wiley, 2002.

The pore volume of the final catalyst monolith is preferably in the range of from 0.05 to 2.0, more preferably 0.1 to 1.5, most preferably 0.2 to 1.2 ml/g.

The pore volume for pores over 50 nm is preferably in the range of 3 to 50%, more preferably 5 to 40% and most preferably 10 to 35%, based on the total pore volume.

The pore size distribution is a further important requirement. In specific embodiments, it can be preferable to obtain a transition alumina catalyst having a multi-modal pore size distribution, for example a bi-modal pore size distribution.

In accordance with this specification, a multimodal pore size distribution means a pore size distribution in which, when incremental pore volume is plotted as a function of pore size, the resulting function exhibits a maximum (or mode) within a first pore size range and a maximum (or mode) within a second pore size range. In general, a maximum (or mode) is the most frequently occurring number within a specific range of numbers. In relation to pore size distribution, the pore size maximum (or mode) is the pore size which, within a specific pore size range or within a subrange falling within such range, corresponds to the highest peak in a graph showing the pore size distribution. Therefore, in accordance with this specification, a multimodal pore size distribution means that within said first pore size range there should be at least one peak in a graph showing the pore size distribution, and within said second pore size range there should also be at least one peak in a graph showing the pore size distribution. Examples are multimodal pore size distributions having two peaks as shown in FIGS. 2 and 3 of EP 2 231 559. The pore size may be the pore diameter or the pore radius.

Preferably, in the multimodal pore size distribution, the pore size range comprises a first pore size range and a second pore size range and the pore sizes in the first pore size range are smaller than the pore sizes in the second pore size range.

Preferably a first pore size range is a pore diameter range of from 0.1 to 50 nm (micropores and mesopores) and a second pore size range is a pore diameter range of greater than 50 nm, for example greater than 50 nm to smaller than 1500 nm (macropores). Preferably the maximum (or mode) in the first pore size range is at a pore diameter of from 5 to 50 nm, more preferably 10 to 30 nm. Further, preferably the maximum (or mode) in the second pore size range is at a pore diameter of from 50 to 1500 nm, more preferably 100 to 1250 nm.

Preferably the pore diameters corresponding to the maximums (or modes) in first and second pore size ranges are separated by at least 200 nm, more preferably at least 300 nm, and by at most 1,500 nm, more preferably at most 1000 nm.

The pore size distribution is determined according to the well-known mercury porosimetry method as described by J. Rouquerol et al. in Pure & Applied Chem., 66(8), 1994, pages 1752 to 1753, using the Washburn equation.

Preferably the catalyst to be used in the present invention has from 3 to 50%, more preferably 5 to 40%, and most preferably 10 to 30%, of the total pore volume in pores having a diameter greater than 50 nm (macropores). Further, preferably the catalyst has from 50 to 97%, more preferably 60 to 95%, and most preferably 70 to 90%, of the total pore volume in pores having a diameter from 0.1 to 50 nm (micropores and mesopores). Still further, preferably the catalyst has less than 3%, more preferably less than 2% and even more preferably less than 1%, of the total pore volume in pores having a diameter greater than 1500 nm. Most preferably, the catalyst has essentially no pore volume in pores having a diameter greater than 1500 nm.

Properties of suitable transition aluminas can be found in Ullmann's Encyclopedia of Industrial Chemistry, 2012, in the section "Aluminum Oxide". Reference can be made to Table 9 thereof. Furthermore, suitable transition aluminas are described in U.S. Pat. No. 7,351,393. Corresponding transition alumina extrudates have for example a pore volume in pores of diameter of over 100 nm, as determined by mercury porosimetry, of at least 0.05 ml/g, a side crushing strength of at least 10 N and a bulk crushing strength of at least 0.1 MPa.

This set of properties can be made available in one material, thereby providing a material with which chemical reactions can be made much more efficient, resulting in higher activity and/or selectivity. Also, this material, when used in fixed bed reactors, provides a decreased pressure drop compared to conventional shaped bodies used in catalysis.

As indicated above, the use of monolith shaped extrudates is important in terms of pressure drop in relation to accessibility of the internal surface of the transition alumina. This also plays a role in eliminating diffusion problems. Another advantageous property of the monolith shaped extrudates is the fact that the ratio of external surface area to volume is more advantageous than in the case of conventional shaped bodies used in catalysis.

Important aspects of the material of the invention are also the strength characteristics. As indicated above a side crushing strength of at least 10 N, preferably at least 20 N, and more preferably at least 30 N, most preferably at least 50 N, specifically at least 100 N and a bulk crushing strength of at least 0.1 MPa are preferred herein. These parameters form the basis for the suitability of the monolith extrudates for use in large scale reactors, like in the chemical and petroleum industry. When the monolith extrudates meet these requirements, they can be used in large fixed bed reactors that require very strong catalysts. The side crushing strength and the bulk crushing strength are defined as follows:

The side crushing strength (SCS) of the catalyst monolith, preferably with dimensions 1.5 cm×1.5 cm×1.2 cm (x,y,z axis, z being the stacking direction), according to the present invention is preferably at least 50 N, more preferably at least 60 N, more preferably at least 100 N, most preferably at least 300 N, when yz or xy opposite planar sides are pressed.

The SCS of shaped bodies is defined as the pressure (in Newtons) at which these are crushed, when treated under pressure.

The determination of the SCS is for examples disclosed in Oil & Gas Science and Technology—Rev. IFP, Vol. 55 (2000), No. 1, pp. 67 to 85, specifically section 3.1.1. An example for the determination of the SCS covering the resistance of a shaped catalyst body to a compressive force is as follows: The shaped body is subjected to a compressive load between jaws. The force required to crush the shaped body is measured and recorded in Newton force. The operation is executed using the semi-automatic Schleuniger Model 6D hardness tester. The shaped body is tested with the YZ or XZ plane facing upright between the measure jaws. Press the "START"-button on the Schleuniger 6D. The jaws will slowly approach each other to execute the crushing test. The crushing strength is displayed on the Schleuniger and the computer monitor.

The maximum SCS depends on the materials used for preparing the catalyst monolith and also on the three-dimensional structure of the catalyst monolith as well as the fiber diameter. The more contact points between the individual fiber layers are present, the higher the side crushing strength will be. Preferably, adjacent layers have at least 10 contact points, more preferably at least 20 contact points, most preferably at least 30 contact points to one neighboring layer. Thus, for a fiber layer, which has two neighboring layers, the number of contact points is twice the number stated above. Due to the contact points, the stack of fiber layers is self-supporting.

There is no upper limit for the SCS of the catalyst monolith. Typically, the maximum SCS is 100,000 N and often it is 10,000 N. Thus, the SCS of the catalyst monolith according to the present invention is preferably in the range of from 60 to 100,000 N, more preferably 100 to 100,000 N and most preferably 300 to 100,000 N.

The maximum can also be the maximum that a machine for measuring SCS is able to measure. The maximum can depend on the size of the monolith. If the monolith is larger than the machine for measuring it allows, the monolith is cut to a suitable size, preferably 1.5 cm×1.5 cm×1.2 cm (xyz axis).

The bulk crushing strength (BCS) of a catalyst is defined as the pressure (in Megapascals) at which 0.5% fines (i.e. particles less than 0.425 mm) are formed when treated under a piston in a tube. For that purpose, 17 ml of shaped catalyst bodies, pre-screened on a 0.425 mm sieve, are loaded in a cylindrical sample tube (diameter 27.3 mm), and 8 ml steel beads are loaded on top. The shaped bodies are subsequently treated at different (increasing) pressures for three minutes, after which the fines are recovered and their percentages are determined. This procedure is repeated until a level of 0.5 wt % fines is reached.

Another aspect of the strength of the material is the attrition, i.e. the amount of material that may break off of the extrudates upon use. This attrition, determined in accordance with ASTM D4058-87, should preferably be less than 7.5 wt %, in particular less than 5 wt %.

The alumina extrudates having the above properties can be prepared by mixing, hydroxide precursor particles or oxyhydroxide precursor particles of transition alumina particles or mixtures thereof, optionally adding a binder and/or a suitable plasticizer in the presence of a liquid, usually water or an aqueous solution of a mineral acid such as hydrochloric, sulfuric, nitric or formic acid, or a base such as ammonia, to form a paste, followed by extruding of the paste in the required form, using a suitable die.

It is possible to use various types of binder materials, such as those based on silica or clays or mixtures thereof. The binder may also be selected from organic materials. Although upon calcination mixed oxides may form, due to the low amount of binder this does not affect the principal character or composition of the monolith.

The amount of binder material in the suspension paste is not more than 20 wt %, preferably in the range of from 0.1 to 15 wt %, more preferably 1 to 10 wt %, and most preferably 2.5 to 5%, based on the amount of hydroxide precursor particles or oxyhydroxide precursor particles of transition alumina particles or mixtures thereof in the suspension paste.

It may furthermore be required to use an organic plasticizer to obtain a uniform mixture and to transform the mixture into a compound with rheological behavior. The plasticizer may be chosen from organic materials such as for example waxes. It is preferred to use a plasticizer that is re-moved during calcination, while providing and maintaining the required strength. The amount of plasticizer used in the preparation of the paste that is to be extruded will vary depending on the type of material and the required properties. Generally, it will not be in excess of 10 wt %, preferably not in excess of 1.5 wt %, more preferably not in excess of 2.5 wt % based on the amount of hydroxide precursor particles or oxyhydroxide precursor particles of transition alumina particles or mixtures thereof.

Preferably, the amount of plasticizer, if applied to the mixture, will not be in excess of 10 wt % based on the total weight of the suspension paste.

The transition alumina particles, hydroxide precursor particles or oxyhydroxide precursor particles thereof or mixtures thereof or the transition alumina catalyst monolith can have a surface acidity as determined by infrared spectroscopy of pyridine adsorption. The surface acidity resulting from Lewis acidic sites may be in the range of from 100 to 2000 µmole/g more preferably 200 to 1200 µmole/g as determined at 180° C. and in the range of from 50 to 1000 µmole/g more preferably 100 to 800 µmole/g as determined at 400° C.

Pyridine FTIR is used to analyze the Bronsted and Lewis acidic sites over a solid catalyst. Pyridine vapor adsorbed on acidic catalysts while Fourier-transform infrared (FTIR) spectra are recorded to show the location of Bronsted (1545 cm-1) and Lewis (1450 cm-1). Spectra may be collected on a Thermo Scientific iS50 FTIR spectrometer equipped with a MCT detector and a Harrack diffuse reflectance high temperature chamber with KBr windows allowing constant N2 gas to flow through. Approximately 40 mg of sample is ground into a fine powder with an agate mortar and transferred into a sample cup. The samples are first dehydrated at 450° C. for 1 hour under flowing dry N2 prior to pyridine adsorption. A spectrum of the sample without pyridine adsorption is collected at 40° C. as background. Then the sample is exposed to pyridine vaper for ~1 minute. The spectra of the sample with pyridine adsorption are collected at 40° C. after the sample were treated at 180 and 400° C. under flowing N2 and maintained for 50 minutes. The difference between the spectra of the sample with and without pyridine is used to quantitatively measure the acidity sites. The peak at ~1545 cm−1 is used to measure Bronsted acid sites and the peak at ~1450 cm−1 is used to measure Lewis acid sites.

The surface acidity of the transition alumina can be adjusted by adding alkali metal hydroxides, alkaline earth metal hydroxides, ammonia, acids, chemical compounds comprising Si or Ti or W, or mixtures thereof to the transition alumina particles, hydroxide precursor particles or oxyhydroxide precursor particles or mixtures thereof or to the suspension paste. For example, alkali or alkaline earth hydroxides such as LiOH, NaOH, KOH, $Mg(OH)_2$, $Ca(OH)_2$, or $Ba(OH)_2$ can be employed as alkaline dopants for lowering the surface acidity of the transition alumina. Likewise, acids and chemical compounds of Si or Ti or W may be applied to enhance the surface acidity.

The addition of acids or bases can also help to gel the transition alumina particles, hydroxide precursor particles or oxyhydroxide precursor particles or mixtures thereof and/or the binder during the preparation of the paste in order to form stable extrudates.

For the transition alumina catalyst, a preferred number average particle size in step a) is in the range of from 0.05 to 700 µm, preferably 0.5 to 500 µm, more preferably 1 to 250 µm.

In this respect, average particle sizes can be measured by sieving the particles or by laser diffraction techniques or by photographic techniques like camsizer techniques. The average particle size refers to the number average particle size or arithmetical average particle size. For irregular particle shapes, the number average maximum particle diameter is measured.

The suspension paste prepared in step a) of the process according to the present invention preferably has a solids content of 1 to 95 wt %, more preferably 10 to 65 wt %.

The 3D robocasting technique employed according to the present invention is well established and can be performed as described in U.S. Pat. Nos. 7,527,671, 6,027,326, 6,401,795, Catalysis Today 273 (2016), pages 234 to 243, or Journal of Catalysis 334 (2016), pages 110 to 115, or U.S. Pat. No. 6,993,406.

The 3D robocasting technique can be used with catalyst formulations which can be based on pastes that are currently used in standard extrusion techniques provided the particle size is small enough to pass the extrusion nozzle. The extrusion formulation or paste contains transition alumina particles, hydroxide precursor particles or oxyhydroxide precursor particles thereof or mixtures thereof. If necessary, a binder and/or a plasticizer can be added to the extrusion mixture.

The robocasting technique implies the extruding through one or more nozzles preferably having a maximum diameter of less than 5 mm, more preferably of less than 1 mm, most preferably less than 0.8 mm. Specifically, the diameter of the nozzle should be in the range of from 0.05 mm to 0.4 mm, most preferably from 0.2 mm to 0.4 mm. The nozzle can have any desired cross-section, e.g. circular, elliptical, square, star-shaped, lobbed. The maximum diameter is the largest diameter of a non-circular cross-section.

One of the main criteria for robocasting is the use of an extrudable paste that has the correct rheological properties for the robocasting technique. The above-mentioned literature gives de-tailed advice as how to obtain the required rheological properties.

If necessary, in the process according to the present invention, a viscosity adjusting agent can be employed. Typical viscosity adjusting agents are celluloses like carboxymethyl cellulose. Preferably, no viscosity adjusting agent or polymer is employed.

The term "porous" employed here defines that the monolith is not a solid block of material but contains channels or pores. By stacking spatially separated catalyst fiber layers in an ABA or ABACA, also referred to as ABC, manner, through-channels or pores can be formed. Thereby, pathways with direct line-of-sight or pathways with no direct line-of-sight can be formed.

The porosity is preferably at least 20%, more preferably at least 30% and can preferably be in the range of from 20 to 90%, and can be determined by nitrogen physisorption, Hg—PV and He-density. It can be determined by the following formula. Porosity (%)=100−[(density of total microextruded structure/density of fiber material)×100]. The density of the total microextruded structure is determined by dividing its total weight by its total volume. The density of the fiber material can be determined by measuring Hg-PV and He-density.

Since the lattices or scaffolds formed from the fibers are self-supporting, open space remains between the fibers which leads to the porosity. Respective structures can be seen in the above-mentioned literature. They show a low pressure drop when employed in a reactor.

The robocasting process employed according to the present invention can also be described as 3D fiber deposition. General description of 3DFD 3D Fiber Deposition (3DFD) is used to shape the powder. The 3DFD method is an adaptive manufacturing method whereby a highly loaded paste is extruded by a moving nozzle. By computer controlling the movement of the extrusion head in x, y and z-direction, a porous material can be produced from the extruded fibers or strands layer by layer. After drying, the porous material can be thermally treated.

The main benefit of this technology is the degree of freedom with regard to the porous parameters (fiber thickness, interfiber distance and stacking design).

The typical flow chart for the 3DFD technology consists of the following subsequent steps:
Prepare highly viscous paste
Extrude through thin nozzle
Computer controlled deposition of fibers to form a porous periodic structure
Drying and if necessary reducing The first important step is to make sure that no large particles are present in the paste. Therefore, the particle size of the starting material is checked. If too large particles are present, the powder is sieved to obtain the desired particle size. As a rule of thumb, the largest particle (re-presented by the D 99 value) should preferably be at least five times smaller than the nozzle size that will be used, more preferably at least ten times smaller.

In the following step the powder is mixed together with the solvent/diluent (e.g. water), if necessary binder and additives such as plasticizers, are added, thus obtaining a viscous paste. A good mixing to achieve a homogenous paste (minimizing agglomerates or the incorporation of air bubbles) is a prerequisite for a smooth and reproducible process. The powder loading of the functional material depends on the specific surface area, the particle size distribution and the powder morphology. Generally, as the particle size of the powder decreases, the viscosity of the paste will increase. Therefore, the solid loading needs to be lowered for these powders. Apart from organic or, preferably, inorganic binder(s), plasticizers can be added to control the rheological behavior of the paste. In some cases a defoamer is also added to avoid air bubbles in the paste.

After mixing and de-airing, the paste is transferred to the paste reservoir and mounted on the 3DFD set-up. The nozzle, preferably either plastic or metal (below 200 µm), is attached to the paste reservoir. Paste extrusion is achieved e.g. by a displacement pump or a screw pump. During deposition, it might be necessary to control the drying conditions.

After drying at room conditions (or under controlled atmosphere and temperature), the 3DFD structure is dried and thermally treated, if necessary. No heat treatment at temperatures above 1000° C. is necessary.

EXPERIMENTAL PROCEDURE OF 3DFD PROCESS

Obtaining a smooth process and a narrow control on the extrusion of thin filaments often re-quires adjustments of both the formulation of the paste and the experimental set-up. The main process parameters which have to be addressed are listed below.
Parameters
Particle size distribution of starting material
Preparation and mixing procedure of the paste
Paste formulation
De-airing & paste reservoir filling
Design of deposition platform
Height control of nozzle
Programming of turns and transition between layers
Tuning extrusion speed versus movement speed
Drying conditions during deposition For a further description of the process, reference can be made to the above-listed documents.

The stacking design is preferably as depicted in FIGS. 1 and 2 of U.S. Pat. No. 7,527,671. Most preferred is a 1-3-1 pattern.

The liquid diluent employed can be chosen from water and organic liquid diluents. Preferably, the liquid diluent contains mainly or is water.

The drying is preferably performed at a temperature in the range of from −100 to 500° C., more preferably 0 to 300° C., most preferably 20 to 150° C.

No treatment of the porous catalyst monolith precursor or porous catalyst monolith at temperatures above 1000° C., preferably above 975° C., more preferably above 925° C., is performed.

The monolith of stacked catalyst fibers is preferably three-dimensionally structured by depositing the extruded fibers in regular, recurring stacking pattern (periodically structured catalyst), to form a three-dimensionally structured porous catalyst monolith precursor.

The monolith can be formed from one continuous extruded fiber or from multiple individual extruded fibers.

Preferably, the regular, recurring stacking pattern is composed of stacked layers of extruded fibers, wherein in each layer at least 50 wt %, more preferably at least 90 wt % of the extruded fibers or each of the fibers are deposited parallel to each other and spatially separated from each other. The parallel deposition can be in straight or curved lines. As an alternative, they can be deposited/stacked in a circular pattern with radial interlayers, like in a cobweb pattern.

More preferably, at least 50 wt %, most preferably at least 90 wt % of the extruded fibers or each of the fibers are deposited as linear strands parallel to each other and spatially separated from each other, wherein the direction of the strands in each layer is different from the direction in neighboring layers, so that a porous structure with contact points of strands of neighboring stacks result. As an alternative, multiple cobweb patterns can be stacked, each pattern layer preferably rotated relative to its neighboring pattern layers.

One example of stacks of layers alternating by 90° in the direction is depicted in FIGS. 1 and 2 of U.S. Pat. No. 7,527,671.

The fibers or strands preferably have a thickness of 10 to 5000 µm, more preferably 10 to 1000 µm, most preferably 150 to 500 µm.

They are preferably spatially separated from each other by 10 to 5000 µm, more preferably 100 to 1000 µm, most preferably 200 to 800 µm.

One example is a stacking of 360 µm strands being spaced by 650 µm.

Typical monolith sizes are 1 mm³ and above, preferably 1 mm³ to 100 m³, more preferably 3 mm³ to 300 m³.

The monolith can have any desired shape. Preferably, it is in the form of a cylinder with circular or ellipsoidal cross section, a cuboid, a sphere, an ellipsoid, a tablet or a polygon.

In comparison to this, typical extrusion processes for transition alumina catalyst extrudates yield extrudates with a minimum diameter of 1.2 mm. Depending on the formulation, these extrudates have a strength of lower than 10 N or lower than 100 N as measured by the SCS method (side crush strength).

Structures made from 360 µm fibers and 650 µm interfiber distance and ABAB or ABC stacking show a side crushing strength of a 1.5 cm-1.5 cm-1.5 cm structure of more than 100 N.

Thus, the process according to the present invention leads to catalyst structures having a high strength combined with high porosity and high geometric surface area and high packing density.

The invention also relates to a three-dimensional porous catalyst monolith of stacked catalyst fibers, obtainable by the above process.

The invention furthermore relates to the use of these monoliths as catalysts in dehydration reactions. Preferably, the reactions involve a gas phase, a liquid phase or mixed liquid/gas phase.

In some embodiments the use of these monoliths as catalysts involves the dehydration of an aliphatic or benzyl alcohol to form an ether or an olefin.

The term "dehydration" encompasses all chemical reactions, in which water is liberated from a chemical compound while forming a covalent bond. Preferably, alcohols or ethers are dehydrated.

In some further embodiments the use of these monoliths as catalysts involves the isomerization of double bonds, cis/trans isomerization and skeletal isomerization reactions.

These reactions are described for example in Ullmann's Encyclopedia of Industrial Chemistry, 2012, in the section "Aluminum Oxide".

The invention furthermore relates to a control system data set containing a plurality of control instructions which when implemented on an additive production facility prompt the additive production facility to produce a three-dimensional porous catalyst monolith or three-dimensional porous catalyst monolith precursor as described above.

Additive production facilities are for example 3D fiber deposition (3DFD), 3D printing, stereolitography, fused filament fabrication (FFF) or laser sintering. These facilities or equipments are used to shape the powder or paste in order to form the three-dimensional catalyst monolith or its precursor. Thus, the additive production facility can be a 3D fiber deposition printer, 3D printer, stereolitography device or laser sintering device. These production facilities or production equipments are typically computer-controlled using a CAD file (computer aided design file). The CAD file contains the information on the three-dimensional structure of the porous catalyst monolith or its precursor and is needed to operate the additive production facility.

This CAD file which can also be described as a control system data set contains a plurality of control instructions which drive the additive production facility, for example the moving nozzle in a 3D fiber deposition apparatus. The control system data set can also be described as control system data record or data drive set. The control system data set or CAD file contains all information necessary to drive the additive production facility in order to produce the monolith or monolith precursor. This meaning is encompassed by the term "prompt" as used above. The control system data set and control instructions are typically electronic data stored on appropriate data storing device which can be a CD, DVD, USB stick, hard drive or SSD drive of a computer or attached to a computer.

The control system data set is typically loaded to the computer controlling the additive production facility prior to printing or extruding the 3D structure. Thus, the term "implementing" typically means loading the control system data or control instructions in a computer system which operates the additive production facility. Thus, the additive production facility then has the control instructions implemented thereon.

The gamma-alumina catalyst monoliths of the present invention show a lower pressure drop, a higher activity and a higher selectivity when compared to normal extrudates. Since more external surface of the catalyst is facing reactants, more of the catalyst is immediately available. Thus, the residence time of the reactant in the catalyst can be shortened due to the faster transport. Consequently, less side products are formed.

The robocasting process allows for the manufacture of three-dimensional porous catalyst monolith structures of stacked catalyst fibers, which have an increased external surface area and/or increased side crushing strength of preferably at least 50 N, more preferably at least 60 N in comparison to normal extrudates.

Furthermore, higher catalyst densities in the reactor can be achieved due to well-ordered stackings of fibers. A packing density of up to 70% is possible by employing regularly stacked catalyst fibers prepared according to the present invention.

The low pressure drop allows to work with smaller fiber diameters compared to single extrudates.

The invention will be further illustrated by the following examples.

Example of 3D Microextruded Catalyst

3D Microextruded Porous Transition Alumina Catalyst Monolith

Suspensions were made from catalyst transition alumina precursor particles, water and acid ($HNO_3$). The ingredients were manually added and mixed to obtain the right rheological properties for extruding through a 400 μm sized nozzle. The particle size of the powder was selected to allow for this extrusion. The suspension is brought in a dispensing unit consisting of a syringe vessel and a nozzle. The unit is mounted on a micro-extruder machine. The micro-extruder is a computer numerical control (CNC) machine that is programmed to move according to a well-defined pattern and within a well-defined form. The CNC machine is programmed to continuously deposit filaments layer by layer in a predefined pattern. The deposition parameters, e.g. the distance between the nozzle and the surface of the structure, the speed of the nozzle movement, the air pressure and the temperature and airflow of the environment, etc. are regulated. A 3D-structure is built in a box by depositing the filaments layer by layer according to the programmed pattern and according to the required dimensions. All 3D structures were afterwards dried at 80° C.

A) A temperature treatment at 850° C. was applied to form a porous transition alumina catalyst monolith. The dimensions of the monolithic structure after calcination were 1.91 cm×1.90 cm×0.74 cm (length, width, height). The porous properties of the monolith were found to be: BET surface area 184 $m^2/g$, total pore volume 0.73 mL/g and SCS>720 N.

B) A temperature treatment of 680° C. was applied to form a porous transition alumina catalyst monolith. Cube-type structures for experimental testing were cut out from a larger monolithic structure. The dimensions of the cube-type structures after calcination were 6.0 mm×6.0 mm×6.0 mm (length, width, height). The porous properties were found to be: BET surface area 217 $m^2/g$, total pore volume 0.74 mL/g. SCS was measured on a representative sample of 2.17 cm×2.17 cm×0.89 cm (length, width, height) and it was found to be 400 N.

C) A temperature treatment of 680° C. was applied to form a porous transition alumina catalyst monolith. Cylinder-type structures for experimental testing were cut out from a larger monolithic structure. The dimensions of the cylinder-type structures after calcination were 2.08 cm×7.0 cm (diameter, total height). The porous properties were found to be: BET surface area 217 m²/g, total pore volume 0.74 mL/g. SCS was measured on a representative sample of 2.17 cm×2.17 cm×0.89 cm (length, width, height) and it was found to be 400 N.

Ethanol Dehydration Experiments

For ethanol dehydration testing of 3D-microextruded alumina catalysts, 25 cc of catalyst was loaded into a 1" OD (0.834" ID)×4 ft stainless steel fixed-bed downflow reactor.

The reactor was equipped with a thermowell that housed five thermocouples.

The reactor was heated by a furnace, with the catalyst loaded such that its location was in the middle furnace section.

Catalyst mass loading was determined by multiplying catalyst bulk density by 25 cc.

In the case of the cubes [Example 1B], an equal volume of inert 14×28 mesh α-alumina granules was loaded with the catalyst and served as interstitial packing.

In the case of the cylinders [Example 1C], bulk density was determined based on normal packing density of cylinder elements with the following nominal dimensions: OD=20.8 mm, ID=5.56 mm, h=16.74 mm with a nominal particle mass of 2.814 g. The cylinders were formed such that they could be stacked single file in the reactor with the thermowell protruding through a center hole which was cut out.

In all cases, ⅛" Denstone spheres were used as bed support and in the pre-heat zone above the catalyst bed to provide surface area for the feedstock to vaporize.

Once loaded, the reactor was purged with 300 sccm $N_2$ for approximately 30 minutes to remove air and subsequently heated to 400° C. under flowing $N_2$ and held for at least 4 hours.

Once pretreatment of the catalyst was completed, the reactor was cooled to 375° C. and pressurized to 118 psig. Once pressure and temperature were stable, N2 flow was stopped and feed consisting of 90 wt % ethanol/10 wt % water was introduced to the reactor at a rate of LHSV$_{EtOH}$=1.926 hr$^{-1}$, where LHSV$_{EtOH}$ is defined as volumetric flow rate of ethanol per catalyst volume. The reactor was held at these conditions for approximately 24 hours.

Product analysis was performed with an online gas chromatograph equipped with a flame ionization detector (FID), a heated sample injection valve, and an HP-PLOT Q capillary column (30 m×0.320 mm×20 μm). The reaction effluent was delivered to the GC through heated sample lines at ~180-200° C. and injected approximately every 15 min.

The following quantities were calculated and used to assess and compare catalyst performance: percent ethanol conversion and percent selectivity to ethylene.

Percent conversion is defined as [(molar flow rate of ethanol in−molar flow rate of ethanol out)/(molar flow rate of ethanol in)]×100.

Percent selectivity is defined as [moles ethylene produced/moles ethanol consumed]×100.

The catalyst [Example 1B] displayed 87.09% conversion and 85.64% selectivity.

The catalyst [Example 10] displayed 78.5% conversion and 56.32% selectivity.

The invention claimed is:

1. A method for producing a three-dimensional porous transition alumina catalyst monolith of stacked catalyst fibers, comprising the following steps:

a) preparing a suspension paste in a liquid diluent of hydroxide precursor particles or oxy-hydroxide precursor particles of transition alumina particles or mixtures thereof and of which suspension can furthermore comprise a binder material selected from organic materials in a maximum amount of 20 wt %, based on the amount of hydroxide precursor particles or oxyhydroxide precursor particles of transition alumina particles or mixtures thereof and/or a plasticizer chosen from organic materials in a maximum amount of 10 wt %, based on the amount of hydroxide precursor particles or oxyhydroxide precursor particles of transition alumina particles or mixtures thereof, all particles in the suspension having a number average particle size in the range of from 0.05 to 700 μm, b) extruding the paste of step a) through one or more nozzles to form fibers, and depositing the extruded fibers to form a three-dimensional porous catalyst monolith precursor, c) drying the porous catalyst monolith precursor to remove the liquid diluent, d) performing a temperature treatment of the dried porous catalyst monolith precursor of step c) at a temperature in the range of from 500 to 1000° C., to form the transition alumina catalyst monolith, wherein no temperature treatment of the porous catalyst monolith precursor or porous catalyst monolith at temperatures above 1000° C. is performed and wherein no further catalytically active metals, metal oxides or metal compounds are applied to the surface of the transition alumina precursor particles, the catalyst monolith precursor or transition alumina catalyst monolith, wherein no dopants are added to the suspension paste and wherein the amount of impurities, selected from $Li_2O$, $Na_2O$, $K_2O$, CaO, MgO, BaO, $B_2O_3$, $Ga_2O_3$, $SiO_2$, $TiO_2$, $ZrO_2$, ZnO, $Fe_2O_3$, as well as chlorides, nitrates and sulfates in the transition alumina particles and hydroxide precursor particles and oxyhydroxide precursor particles thereof, is not higher than 2.5 wt %, based on the transition alumina in the monolith.

2. The method of claim 1, wherein transition alumina is the sole phase forming the catalyst monolith.

3. The method of claim 1, wherein the transition alumina is eta-, gamma- or delta-alumina, and wherein eta-, gamma- and/or delta-alumina particles are present in the suspension paste; and/or wherein gibbsite, bayerite, nordstrandite, doyleite, diaspore, boehmite, pseudoboehmite, akdalaite or tohdite, or mixtures thereof are present in the suspension paste and wherein in step d) a temperature treatment in the range of from 500 to 925° C. is performed to effect the transformation.

4. The method of claim 1, wherein in step b) the nozzles have a maximum diameter of less than 5 mm.

5. The method of claim 1, wherein the monolith of stacked catalyst fibers is three-dimensionally structured by depositing the extruded fibers in a regular, recurring stacking pattern to form a three-dimensionally structured porous catalyst monolith precursor.

6. The method of claim 1, wherein the monolith is formed from one continuous extruded fiber or from multiple individual extruded fibers.

7. The method of claim 1, wherein the regular, recurring stacking pattern is composed of stacked layers of extruded fibers, wherein in each layer at least 50 wt % of the extruded fibers are deposited parallel to each other and spatially separated from each other, or in a cobweb pattern.

8. The method according to claim 7, wherein at least 50 wt % of the extruded fibers are deposited as linear strands parallel to each other and spatially separated from each other, or wherein multiple cobweb patterns are stacked, wherein the direction of the strands in each layer is different from the direction in neighboring layers, so that a porous structure with contact points of strands of neighboring layers results.

9. The method according to claim 1, wherein the transition alumina particles, hydroxide precursor particles or oxyhydroxide precursor particles or mixtures thereof or the transition alumina catalyst monolith have an acidity in the range of from 100 to 2000 μmol/g.

10. The method according to claim 1, wherein the transition alumina catalyst monolith consists of eta-, gamma- or delta-alumina, or mixtures thereof.

11. The method of claim 1, wherein the transition alumina catalyst monolith has a BET surface area in the range of from 50 to 350 m$^2$/g.

12. The method according to claim 1, wherein the transition alumina catalyst monolith has a porosity of at least 20%, determined by nitrogen physisorption.

13. The method according to claim 1, wherein the transition alumina catalyst monolith has a pore volume in the range of from 0.05 to 2.0 ml/g, determined by mercury porosimetry measurements.

14. The method according to claim 1, wherein the transition alumina catalyst monolith contains no dopants and the content of impurities is below 0.1 wt %.

15. The method according to claim 1, wherein the transition alumina catalyst monolith has a monomodal or polymodal pore size distribution.

16. A three-dimensional porous catalyst monolith of stacked catalyst fibers, obtainable by the method according to claim 1.

17. The monolith according to claim 16, which has a side crushing strength of at least 60 N, determined as disclosed in Oil and Gas Science and Technology-Riv. IFP, vol 55 (2000) No 1, pages 67-85.

18. A dehydration reaction which comprises utilizing the three-dimensional porous transition alumina catalyst monolith of stacked catalyst fibers according to claim 16.

19. The reaction according to claim 18, wherein methanol, ethanol, n-propanol, iso-propanol, n-butanol, iso-butanol, tert-butanol, pentanol, hexanol, 1-phenylethanol, 2-phenylethanol, cumyl alcohol (2-phenyl-2-propanol) or glycerol are dehydrated.

20. A process for the isomerization of double bonds, cis/trans isomerization and skeletal isomerization reactions utilizing the three-dimensional porous transition alumina catalyst monolith of stacked catalyst fibers according to claim 16.

21. A method for producing a three-dimensional porous transition alumina catalyst monolith of stacked catalyst fibers, comprising the following steps:
 a) preparing a suspension paste in a liquid diluent of hydroxide precursor particles or oxy-hydroxide precursor particles of transition alumina particles or mixtures thereof and which suspension can furthermore comprise a binder material selected from organic materials in a maximum amount of 20 wt %, based on the amount of hydroxide precursor particles or oxyhydroxide precursor particles of transition alumina particles or mixtures thereof and/or a plasticizer chosen from organic materials in a maximum amount of 10 wt %, based on the amount of hydroxide precursor particles or oxyhydroxide precursor particles of transition alumina particles or mixtures thereof, all particles in the suspension having a number average particle size in the range of from 0.05 to 700 μm,
 b) extruding the paste of step a) through one or more nozzles to form fibers, and depositing the extruded fibers to form a three-dimensional porous catalyst monolith precursor,
 c) drying the porous catalyst monolith precursor to remove the liquid diluent,
 d) performing a temperature treatment of the dried porous catalyst monolith precursor of step c) at a temperature in the range of from 500 to 1000° C., to form the transition alumina catalyst monolith,
 wherein no temperature treatment of the porous catalyst monolith precursor or porous catalyst monolith at temperatures above 1000° C. is performed and
 wherein no further catalytically active metals, metal oxides or metal compounds are applied to the surface of the transition alumina precursor particles, the catalyst monolith precursor or transition alumina catalyst monolith,
 wherein no dopants are added to the suspension paste and wherein the amount of impurities, selected from Li$_2$O, Na$_2$O, K$_2$O, CaO, MgO, BaO, B$_2$O$_3$, Ga$_2$O$_3$, SiO$_2$, TiO$_2$, ZrO$_2$, ZnO, Fe$_2$O$_3$, as well as chlorides, nitrates and sulfates in the transition alumina particles and hydroxide precursor particles and oxyhydroxide precursor particles thereof, is not higher than 2.5 wt %, based on the transition alumina in the monolith;
 wherein the transition alumina catalyst monolith has a BET surface area in the range of from 50 to 350 m$^2$/g.

22. The method according to claim 21, wherein the transition alumina catalyst monolith has a porosity of at least 20%, determined by nitrogen physisorption.

23. A method for producing a three-dimensional porous transition alumina catalyst monolith of stacked catalyst fibers, comprising the following steps:
 a) preparing a suspension paste in a liquid diluent of hydroxide precursor particles or oxy-hydroxide precursor particles of transition alumina particles or mixtures thereof and which suspension can furthermore comprise a binder material selected from organic materials in a maximum amount of 20 wt %, based on the amount of hydroxide precursor particles or oxyhydroxide precursor particles of transition alumina particles or mixtures thereof and/or a plasticizer chosen from organic materials in a maximum amount of 10 wt %, based on the amount of hydroxide precursor particles or oxyhydroxide precursor particles of transition alumina particles or mixtures thereof, all particles in the suspension having a number average particle size in the range of from 0.05 to 700 μm,
 b) extruding the paste of step a) through one or more nozzles to form fibers, and depositing the extruded fibers to form a three-dimensional porous catalyst monolith precursor,
 c) drying the porous catalyst monolith precursor to remove the liquid diluent,
 d) performing a temperature treatment of the dried porous catalyst monolith precursor of step c) at a temperature in the range of from 500 to 1000° C., to form the transition alumina catalyst monolith,
 wherein no temperature treatment of the porous catalyst monolith precursor or porous catalyst monolith at temperatures above 1000° C. is performed and
 wherein no further catalytically active metals, metal oxides or metal compounds are applied to the surface of the transition alumina precursor particles, the catalyst monolith precursor or transition alumina catalyst monolith, wherein no dopants are added to the suspension paste and wherein the amount of impurities, selected from $Li_2O$, $Na_2O$, $K_2O$, CaO, MgO, BaO, $B_2O_3$, $Ga_2O_3$, $SiO_2$, $TiO_2$, $ZrO_2$, ZnO, $Fe_2O_3$, as well as chlorides, nitrates and sulfates in the transition alumina particles and hydroxide precursor particles and oxyhydroxide precursor particles thereof, is not higher than 2.5 wt %, based on the transition alumina in the monolith;

wherein the transition alumina catalyst monolith has a porosity of at least 20%, determined by nitrogen physisorption.

* * * * *